United States Patent [19]

Morimoto

[11] Patent Number: 5,171,220
[45] Date of Patent: Dec. 15, 1992

[54] DUAL-CHAMBER TYPE SYRINGE

[75] Inventor: Shuji Morimoto, Osaka, Japan

[73] Assignee: Takeda Chemical Industries, Ltd., Osaka, Japan

[21] Appl. No.: 821,778

[22] Filed: Jan. 16, 1992

[30] Foreign Application Priority Data

Jan. 16, 1991 [JP] Japan .................. 3-3407

[51] Int. Cl.[5] ............................ A61M 37/00
[52] U.S. Cl. ...................... 604/88; 604/270; 604/414
[58] Field of Search ............ 604/87, 88, 220, 200, 604/415, 416, 414, 412, 413

[56] References Cited

U.S. PATENT DOCUMENTS

| 3,397,694 | 8/1968 | Ogle . | |
|---|---|---|---|
| 3,810,469 | 5/1974 | Hurschman | 604/88 |
| 3,828,775 | 8/1974 | Armel | 604/200 |
| 3,872,864 | 3/1975 | Allen, Jr. . | |
| 3,890,971 | 6/1975 | Leeson et al. | 604/220 |
| 4,031,895 | 6/1977 | Porter | 604/88 |
| 4,055,177 | 10/1977 | Cohen . | |
| 4,059,109 | 11/1977 | Tischlinger . | |
| 4,296,786 | 10/1981 | Brignola . | |
| 4,328,802 | 5/1982 | Curley et al. . | |
| 4,516,967 | 5/1985 | Kopfer . | |
| 4,568,346 | 2/1986 | Dijk | 604/88 |
| 4,581,016 | 4/1986 | Gettig | 604/88 |
| 4,589,879 | 5/1986 | Pearson | 604/88 |
| 4,592,744 | 6/1986 | Jagger et al. . | |
| 4,613,326 | 9/1986 | Szwarc . | |
| 4,619,651 | 10/1986 | Kopfer et al. | 604/87 |
| 4,624,667 | 11/1986 | Rutnarak | 604/414 |
| 4,722,271 | 9/1988 | Meyer et al. | 604/200 |
| 4,941,876 | 7/1990 | Meyer et al. | 604/416 |
| 4,994,029 | 2/1991 | Rohrbough | 604/88 |

Primary Examiner—Paul J. Hirsch
Attorney, Agent, or Firm—Wenderoth, Lind & Ponack

[57] ABSTRACT

A disposable syringe of a dual-chamber type, wherein an injection needle is secured to the tip end of an injection cylinder with a first component being filled in it, and the injection cylinder is accommodated for its free sliding operation within a cylindrical housing, a second component container is air tightly secured to the tip end of the housing through a seal member through which a penetrating operation can be effected, and a cover for air tightly covering the injection cylinder rear end portion, including a plunger which is inserted for its free sliding operation into the injection cylinder in cooperation with the housing is engaged with the rear end of the housing.

8 Claims, 17 Drawing Sheets

DUAL-CHAMBER TYPE SYRINGE

BACKGROUND OF THE INVENTION

The present invention relates to a a disposable type syringe where two components, for example, a solid medicine and a liquid solvent are previously filled respectively into separate dual-chambers.

Conventionally powdered medicine, liquid solvents and injection cylinder are normally used when powdered injection medicines are given. The powdered medicines are filled aseptically into a vial or an ampule container. As liquid solvents, distilled water for injection or an isotonic sodium chioride solution are filled aseptically in an ampule or the like. A so-called disposable syringe of a disposable type is overwhelmingly used nowadays from a point view of safety as an injection cylinder.

The injection against to human body or the like is effected with the following procedure. They are taken out of sealed bags or outer boxes. A disposable injection needle is mounted on a disposable syringe, and the neck portion of an ampule with a liquid solvent being contained in it is cut. The solvent is aspirated with a disposable syringe with a needle attached to it. Then, the injection needle of the disposable syringe is penetrated through the rubber stopper of a vial with powdered medicine being contained in it so as to inject the liquid solvent into the interior thereof. The powdered medicine is sufficiently dipped, dissolved into the liquid solvent in the vial. Thereafter, the solution is aspirated, picked into an injection cylinder to draw out the air so that the injection is effected.

This is a conventional injection operation normally effected. This operation takes more time, with a problem even in terms of cost, and contamination of glass pieces at ampule break time.

As a method of solving such problems, a dual-chamber type of prefilled syringe is found out. But in the present time point, the demand in this type of syringe is not satisfied completely.

These requirements are as follows.

1. Both powdered medicine and liquid solvent must be heremetically sealed and kept in a sterile condition until ready for injection.
2. It must provide for safe sealing of the material to prevent accidental mixture before time for use.
3. The integrity of the system should be preserved to prevent contamination of the material from outside sources, including the atmosphere during storing, mixing and injection.
4. The injection needle must be kept sterile until injection is effected.
5. The syringe must be compact and completely packaged in a single unit before use.
6. It must provide for adequate mixing and dissolving of the materials.
7. It must be simple and operable by medical personel in a conventional manner.
8. It must be simple and economical to manufacture.
9. It must be rigid and capable of withstanding shipment and handling by personnel.
10. The combination of medicament, diluent, rubber and glass should not combine to cause a particulate matter problem.
11. Once activated the unit should provide drug stability and pharmacological potency at room temperatures for at least eight hours.
12. It should not be subject to accidental activation, contamination, malfunction or disassembly.
13. It should have product stability capable of going to two years.
14. It must not require abnormal storage condition or handling.
15. It must have all components pre-attached so that no assembly is required for use.
16. The need to remove any parts prior to use should be minimal.
17. It should be capable of adapting to existing manufacturing process, knowledge and skills, including filling equipment.
18. It should be functional with presently approved rubber compound formulations.

Proposals for satisfying some of the above described demand items are already made. The representative ones are as follows.

A. U.S. Pat. No. 3,872,864

In the arrangement of U.S. Pat. No. 3,872,864, a tube on the outer side and a tube on the inner side are provided. The tube on the inner side has a rubber plunger secured onto a single side so as to play a role of the plunger as a whole with respect to the tube on the outer side. The plunger side of the tube tip end on the inner side has a rubber packing provided with a slit being formed at the center. A plunger with respect to the inner side tube is inserted onto the opposite side. Solid medicines are provided in the closed space formed within the outer side tube. Liquid medicine or liquid solvent is filled into the closed space formed with the inner side tube. The slit of the rubber packing is opened with water pressure by the advancing operation of the plunger of the tube on the inner side. The liquid is fed into the tube on the outer side so as to effect the mixing, dissolving operations of these medicines.

B. U.S. Pat. No. 4,055,177

In the arrangement of U.S. Pat. No. 4,055,177, the syringe interior is separated with first, second and third rubber seal materials. Solid medicine is filled into the closed space formed with a syringe tip end sealed with the rubber packing and a first rubber seal material. A needle is disposed in the first rubber seal material with a needle tip end being directed towards a second rubber seal material. A liquid solvent is filled in the closed space formed between the second and the third rubber seal materials. In the construction, the third rubber seal material is depressed against the second rubber seal material side with a plunger method. The second, first rubber seal materials are moved onto the syringe tip end side, and the needle of the first rubber seal material is thrust through the second rubber seal material so that solution is fed through the needle onto the solid medicine side. Therefore, the mixing, dissolving operations are effected.

C. U.S. Pat. No. 4,059,109

In the arrangement of U.S. Pat. No. 4,059,109, the syringe interior is divided into the first, second and third rubber seal materials as in the above U.S. Patent B. Needles are respectively buried in the first, second rubber seal materials. Both the rubber layers are adapted to be thrust with these needles with the outer pressure.

The solid medicine is filled in the closed space formed between the first and second rubber seal materials. Liquid solvent is filled in the closed space formed between the second and third rubber seal materials. In the construction, the third rubber seal material is pushed onto the second rubber seal material side with a plunger rod. The second and first rubber seal material moves onto the syringe tip end side, and the needle of the second seal material is thrust into a rubber layer so as to feed the solution onto the solid medicine side through the needle. Therefore, the mixing, dissolving operations are effected.

D. U.S. Pat. No. 4,613,326 (Japanese Laid-Open Patent Application Tokaisho No. 62-14863)

In the arrangement of U.S. Pat. No. 4,613,326, a small groove shaped passage extending in the syringe longitudinal direction is formed in one location on the side face of the syringe. The syringe interior is divided with the first, second rubber seal materials. The small groove shaped passage is positioned between the first seal material and the syringe tip end. A solid medicine is filled in the closed space formed between the syringe tip end sealed with the rubber packing and the first seal material. The liquid solvent is filled in the closed space to be formed between the first and second seal materials. In the construction, the second seal material is pushed onto the first seal material side with the plunger rod so as to stop with the small groove shaped passage portion so that the respective closed space is connected with each other through the small groove shaped passage. The solution is fed onto the solid medicine side so as to effect mixing, dissolving operations.

E. U.S. Pat. No. 4,328,802

In the arrangement of U.S. Pat. No. 4,328,802, the needle tip of needle attached syringe with a liquid solvent being filled in it is thrust into the rubber plug portion of a vial with a solid medicine being filled in it so as to effect a seal operation. Adapters are engaged with both a vial head portion and the needle side portion of the syringe so as to connect the adapters with each other. The mutual positional relation of the vial and the syringe is adapted to be retained so that the sealing operation is effected with an injection needle of the syringe being half thrust into the rubber plug of the vial by a stopper member positioned between these adapters. In the giving preparation, the intermediate stopper is removed, the syringe is pressed against the vial side. The injection needle is thrust through the rubber plug to connect the syringe interior with the vial by pushing of the syringe against the vial side so as to inject the liquid solvent into the vial interior. Therefore, the resolution is obtained.

F. U.S. Pat. No. 4,516,967

In the arrangement of U.S. Pat. No. 4,516,967, the needle tip of the needle attached syringe with a liquid solvent being filled in it is thrust into the rubber plug portion of the vial with a solid medicine being filled in it so as to effect the sealing operation as shown in the above U.S. Patent E. Fixing, positioning operations are effected with an hollow tube so as to surround both of the vial head portion and the needle side portion of the syringe. The positioning and fixing of the hollow tube and the syringe, and the sealing are effected with the engagement between the tube inner diameter and the syringe outer diameter and the sealing with the tape. The positioning and fixing of the hollow tube and the vial, and sealing are effected with the engagement between the tube and the vial, and the engagement with a metal material. Also, the relative position between the syringe and the vial is movable with the improvement in the hollow tube. In the prescribing preparation, the needle is thrust into the rubber plug by the pressing of the syringe against the vial side, so that the needle thrusts through the rubber plug so as to connect the syringe interior with the vial, so that the mixing, dissolving operation is effected.

The above described conventional dual-chamber type of prefilled syringe has following problems.

As the arrangement shown in U.S. Patent A has construction where a solid medicine and a liquid are separated by rubber packing having a slit, with a problem that the solid medicine and the liquid solvent are not completely separated. As the inner side tube as it is is not fixed sufficiently, armored parts are further required at the transportation or storage time.

As the solid medicine and the liquid solvent are required to be filled within the same syringe in the arrangement shown in U.S. Patent B, the manufacturing operation is generally not easy, and the terminal sterilization of the liquid solvent is impossible to effect. As the third seal material is not fixed sufficiently as it is, armored parts are required especially at the transportation and storage time.

As the solid medicine and the liquid solvent are required to be filled within the same syringe as in U.S. Patent B in the arrangement of U.S. Patent C, the manufacturing operation is not generally easy and the terminal sterilization of the liquid solvent is impossible to effect. Further, second, third needle buried seal materials or the like lack in simplicity, with a problem that the manufacturing operation is difficult to effect even in this point.

According to the arrangement shown in U.S. Patent D, the solid medicine and the liquid solvent are required to be filled similarly within the same syringe, so that the manufacturing operation is not easy and the terminal sterilization of the liquid solvent is also impossible to effect. As the solid medicine and the liquid solvent exist across one rubber seal, the contermination is a problem in terms of complete separation. Further, an injection needle and a plunger rod are required to be mounted, an assembling operation is required with a problem of more time. As the fixing of the inner side tube is not sufficient as it is, the armored parts are required especially at the transportation, storage time.

As the air tightness property of the respective adapters and the vials or the syringe are not complete in the arrangement of U.S. Patent E, with a problem in terms of the aseptic assurance of the injection needle. Also, the plunger rod is required to be mounted, which requires more time. As the terminal sterilization of the liquid solvent is impossible to effect. The mounting of the intermediate stopper portion as it is is not sufficient in strength. Therefore, armored parts are required especially at transportation and storage time.

In the arrangement of U.S. Patent F, the air tightness of the hollow tube and the syringe depends upon the tape seal. Due to its shape, the terminal sterilization of the solution is impossible to effect.

As described hereinabove, any one of the dual-chamber type prefilled syringes proposed conventionally does not meet many of the above described demands and are not utilized widely.

SUMMARY OF THE INVENTION

Accordingly, the present invention has been developed with a view to substantially eliminating the above discussed drawbacks inherent in the prior art and has for its essential object to provide an improved dual-chamber type of disposable syringe.

Another important object of the present invention is to provide an improved dual-chamber type of disposable syringe, which can satisfy most of the demand items of this type of injector and is rich in utility.

In accomplishing these and other objects, the dual-chamber type syringe of the present invention comprises an injection cylinder where an injection needle is secured to the needle holder of its tip end, a plunger is inserted for its free sliding operation from the rear end opening portion, and a first component is filled inside, a cylindrical housing wherein the tip end portion of the injection cylinder is inserted for its free sliding operation from the rear end opening portion of the housing, seal members which can thrust through the tip end opening are engaged, a second component container which is air tightly engaged with the tip end portion of the housing across the above seal member and has therein a second component, a cover which is engaged detachably with the rear end opening portion of the housing, and covers air tightly the injection cylinder and the plunger in cooperation with the housing.

A further desirable embodiment of the present invention is a disposable dual-chamber type syringer where two components, one is a liquid and the other is a medicine, are accommodated separately, injection is effected with these two components being mixed with each other, comprising a cylindrical housing provided on one side with a second mounting portion and on the other side with a first mounting portion and a third mounting portion, with the first mounting portion and the second mounting portion being communicated with each other, a second component container being secured through the seal member onto the second mountain portion of the housing with the second component being air tightly sealed through a seal material capable of penetrating, an injector, composed of an injection cylinder for enclosing the first component in, an injection needle capable of penetrating a plunger to be slidable and the above seal material, being engaged with the first mounting portion of the above housing, for its possible displacement from a first position to a second position through a guide means, a cover secured onto a third mounting portion of the above housing so as to air tightly cover the above injector and breakable with depressing pressure when the above plunger is operated, wherein the second component and the first component are individually accommodated in the air tightly sealing condition respectively within the above second component container and the injection cylinder, the above cover is broken during the using operation to displace the plunger of the injector from the first position to the second position so that the injection needle is penetrated by thrusting through the seal material of the second component container, the second component of the second component container is adapted to mix with the first component of the injection cylinder through the injection needle.

Also, the above guide means is composed of one-stage and two-stage ribs arranged in series for engagement of the injector, the injector is retained in the first position with the one-stage rib with the contact condition being changed with respect to the injector of both the ribs, the injection cylinder is adapted to be retained in the second position with the two-stage rib when the injector is displaced into the two-stage rib from the one stage.

The first component within the injection cylinder and the second component within the second component chamber are air tightly accommodated respectively, separately within the container and cylinder, and are separated mutually with seal members. The sealing property of each component and the non-mixing property before the use are achieved. The terminal sterilization can be effected as described later and the filling of the component is easy in the manufacturing without contamination possibility of the foreign matters. The injection cylinder including the injection needle secured to its tip end is retained wholly air tightness within the chamber consisting of the outer portion of the yousing and the cover. The positional relation of each portion is not changed with the influence from the outside. Therefore, the armored parts are not required.

The terminal sterilization in the construction of the present invention can be achieved through high pressure steam sterilization by an autoclave or the like, for example, after the filling of the second component into the second component container. When the first component is a powered medicine, it is desirable that the respective chambers should be completely separated especially for prevention of the stability deterioration caused by moisture absorption. Especially the seal members such as rubber stopper and so on after the steam sterilization thereof are extremely difficult in complete drying, the complete separation of the respective container and cylinder as in the construction of the present invention is significant.

In the prescribing preparation, the cover is forcebly pressed to separate, and the plunger and the housing are depressed onto the tip end side of the housing. After the seal members have been thrust with an injection needle, the plunger is restored so as to suck into the injection cylinder the liquid component placed within the second component container for mixing it with the first component. In this condition, the injection cylinder is drawn out of the housing so as to complete the prescribing preparation.

BRIEF DESCRIPTION OF THE DRAWINGS

These and other objects and features of the present invention will become apparent from the following description taken in conjunction with the preferred embodiment thereof with reference to the accompanying drawings, in which.

DETAILED DESCRIPTION OF THE INVENTION

Figure 1:
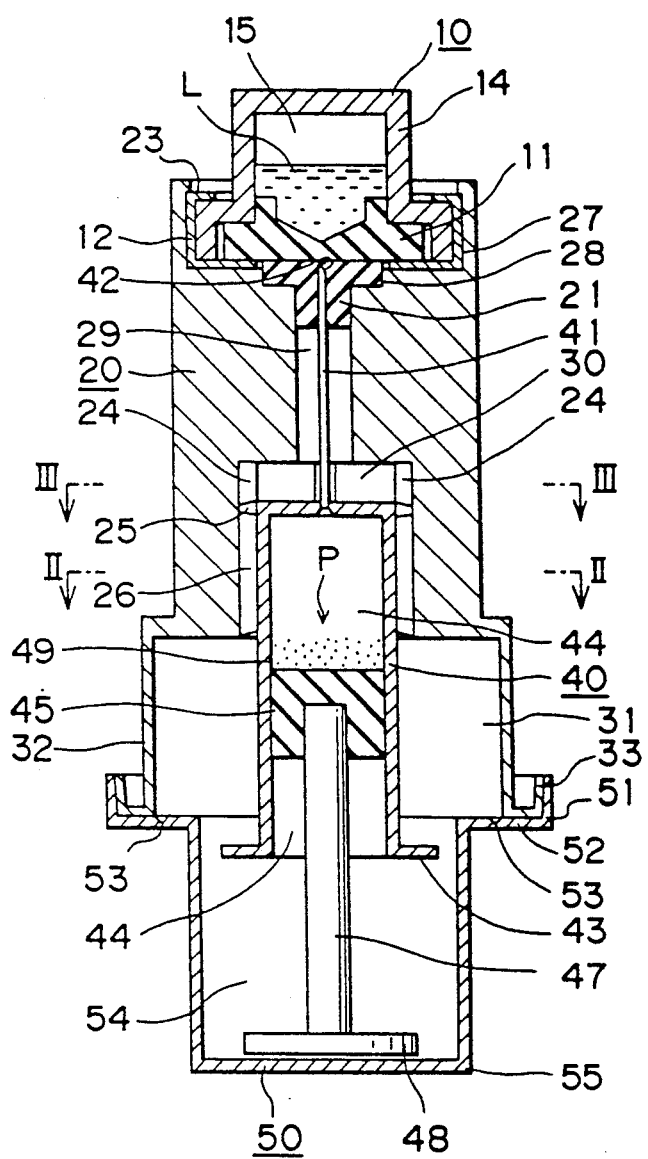
FIG. 1 is a longitudinal sectional view showing, in a storage condition, the construction of one embodiment of a dual-chamber syringe of the present invention.
Figure 2:
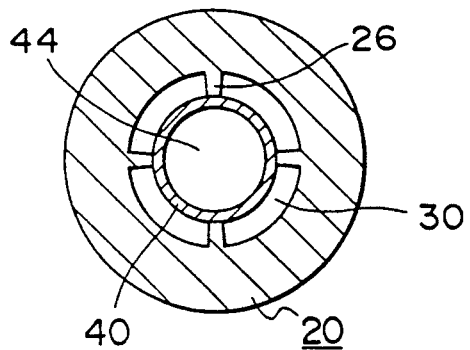
FIG. 2 is a sectional view in the II—II of FIG. 1.
Figure 3:
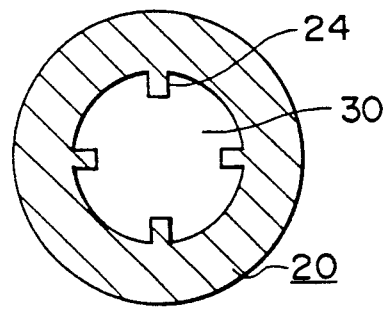
FIG. 3 is a sectional view in the III—III of FIG. 1.
Figure 4:
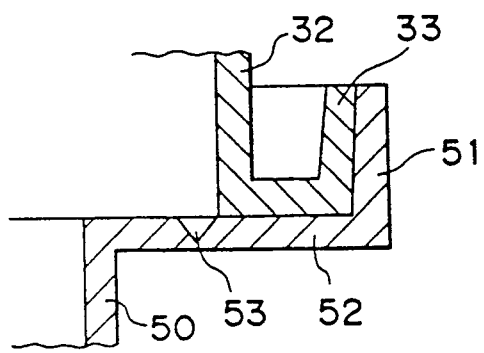
FIG. 4 is an enlarged sectional view of one portion of FIG. 1.

Before the description of the present invention proceeds, it is to be noted that like parts are designated by like reference numerals throughout the accompanying drawings.

One embodiment of a dual-chamber type syringe in the present invention will be described hereinafter with reference to the drawings.

Figure 5:
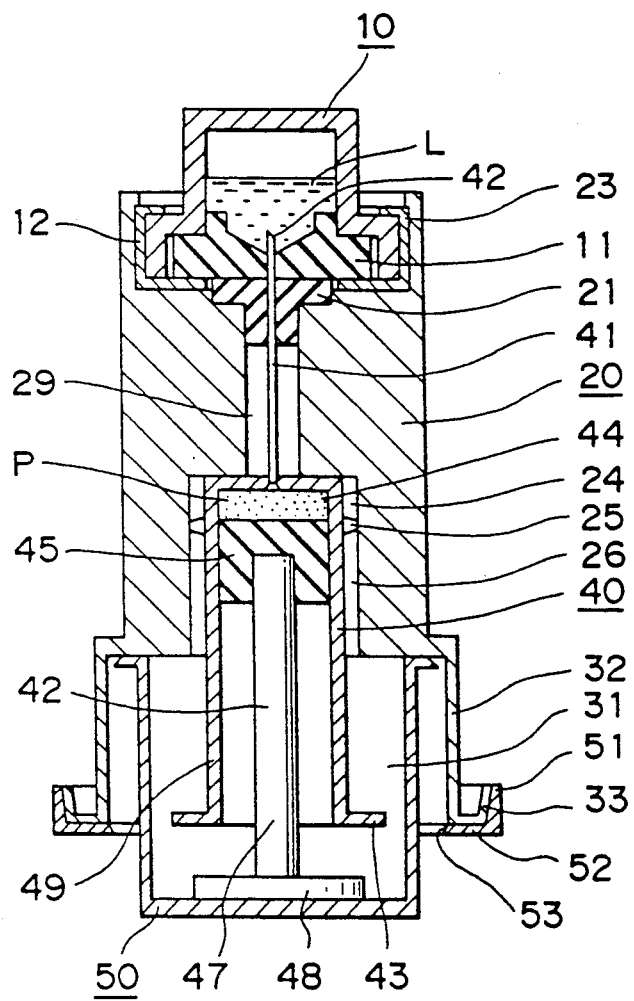
FIG. 5 is an illustration view of a first procedure using the embodiment shown in FIG. 1, a longitudinal sectional view showing a condition where a plunger and an injection cylinder are depressed with a cover being broken.
Figure 6:
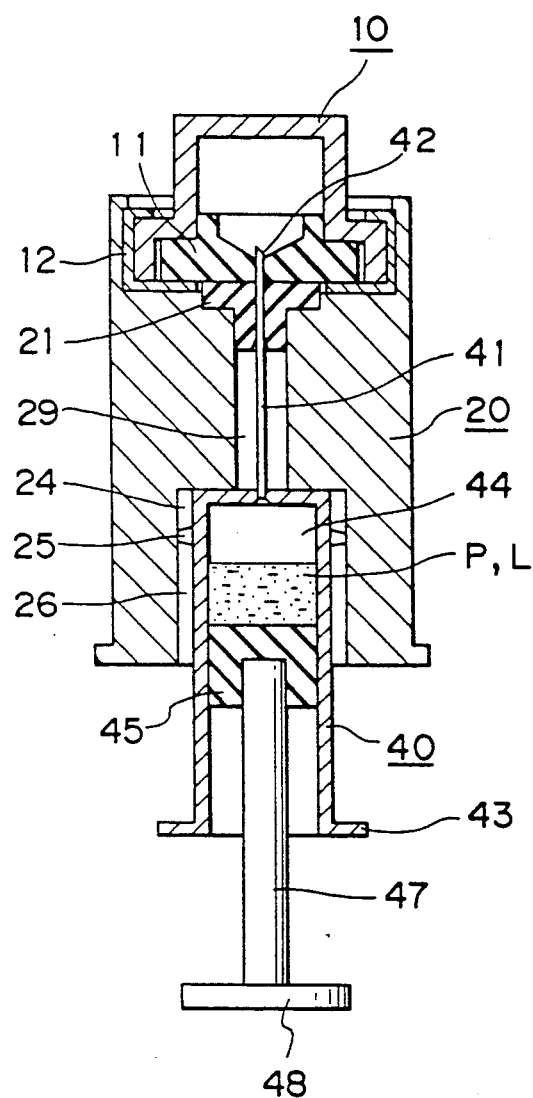
FIG. 6 is also an illustrating view of a second procedure using the embodiment shown in FIG. 1, a longitudinal sectional view showing a condition wherein the plunger is restored, the liquid component is sucked into the injection cylinder.
Figure 7:
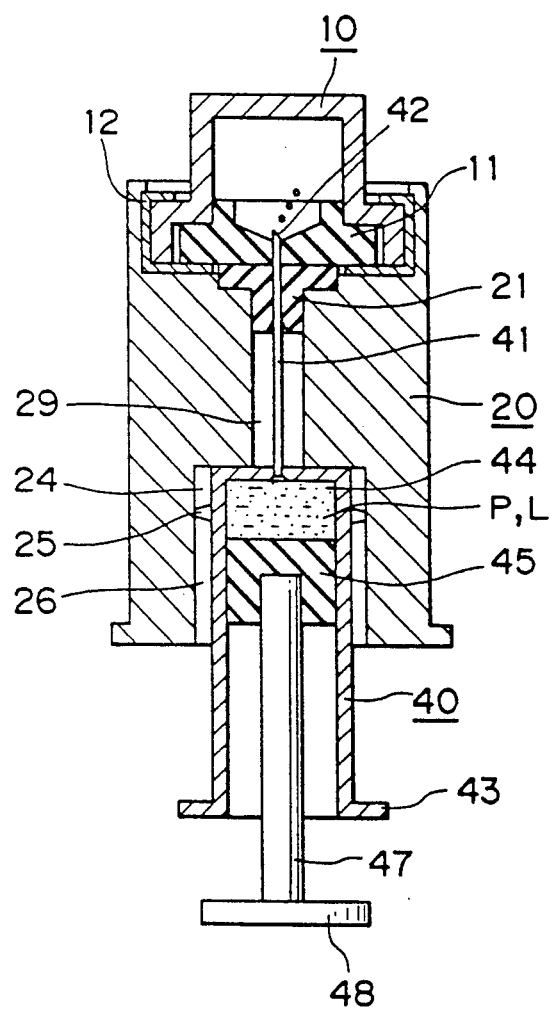
FIG. 7 is an illustrating view of a third procedure using the embodiment shown in FIG. 1, a longitudinal sectional view in a condition within the air within the injection cylinder is drawn out.
Figure 8:
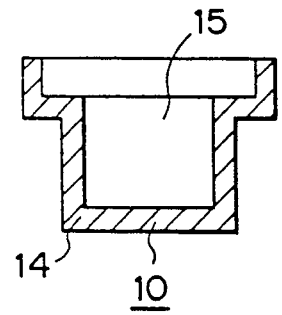
FIG. 8 is a sectional view showing a first step of assembling a second composing container in the embodiment of FIG. 1.
Figure 9:
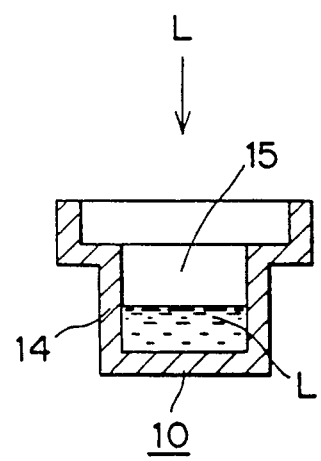
FIG. 9 is a sectional view showing a second step of assembling a second component container in the embodiment in FIG. 1.
Figure 12:
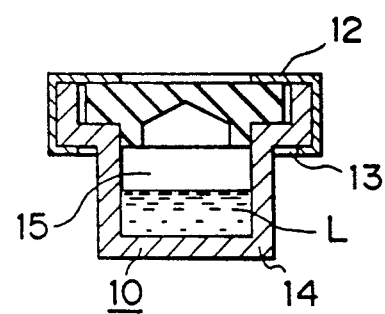
FIG. 12 is a sectional view showing a fifth step of assembling the second component container in the embodiment of FIG. 1.
Figure 10:
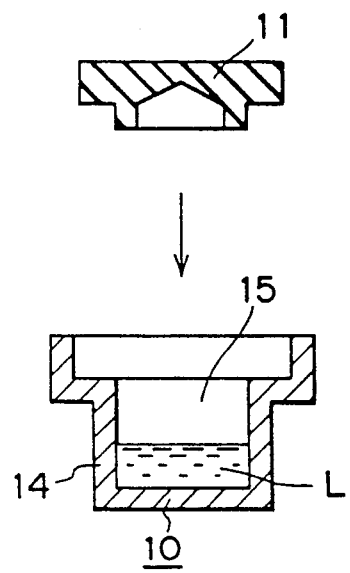
FIG. 10 is a sectional view showing a third step of assembling the second component container in the embodiment of FIG. 1.
Figure 11:
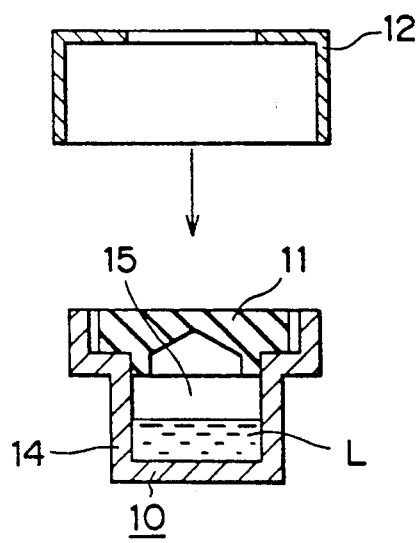
FIG. 11 is a sectional view showing a fourth step of assembling the second component container in the embodiment of FIG. 1.
Figure 13:
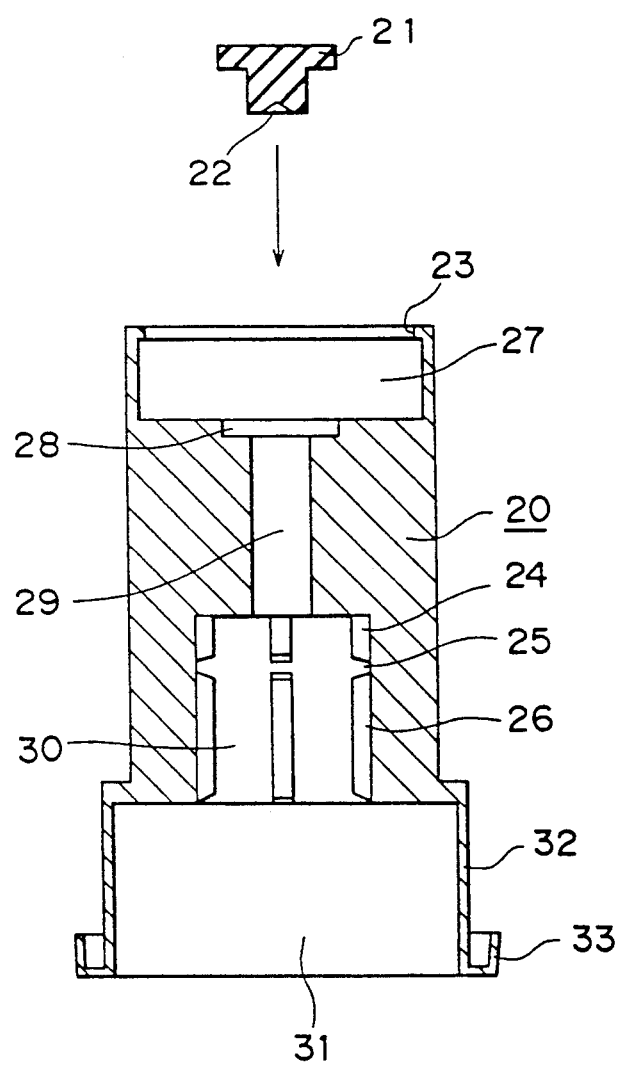
FIG. 13 is a sectional view showing a first step of assembling the second component container to a housing in the embodiment of FIG. 1.
Figure 14:
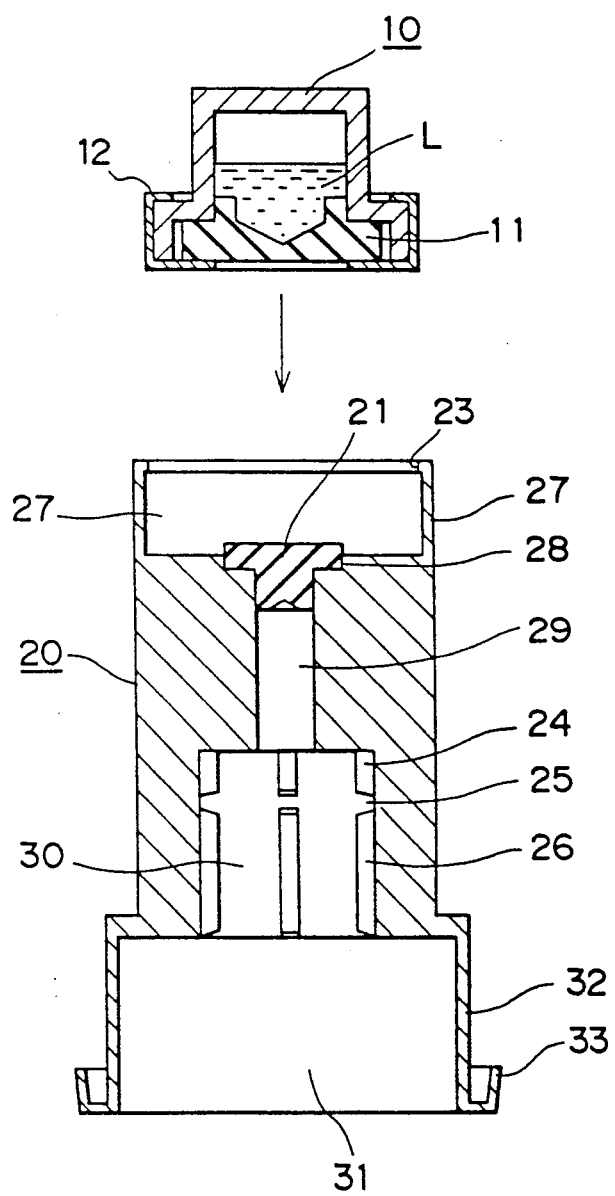
FIG. 14 is a sectional view showing a second step of assembling the second component container to the housing in the embodiment of FIG. 1.
Figure 15:
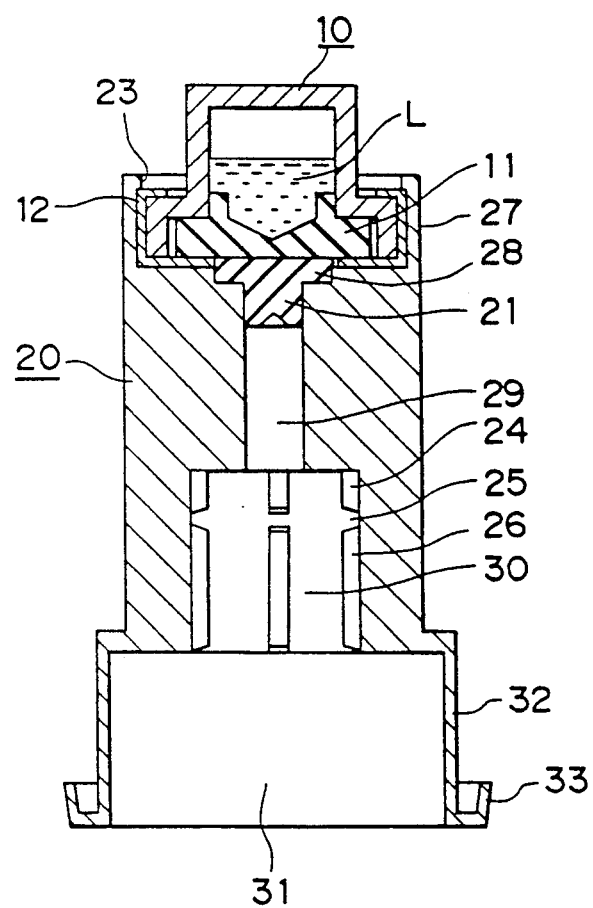
FIG. 15 is a sectional view showing a third step of assembling the second component container to the housing in the embodiment of FIG. 1.
Figure 16:
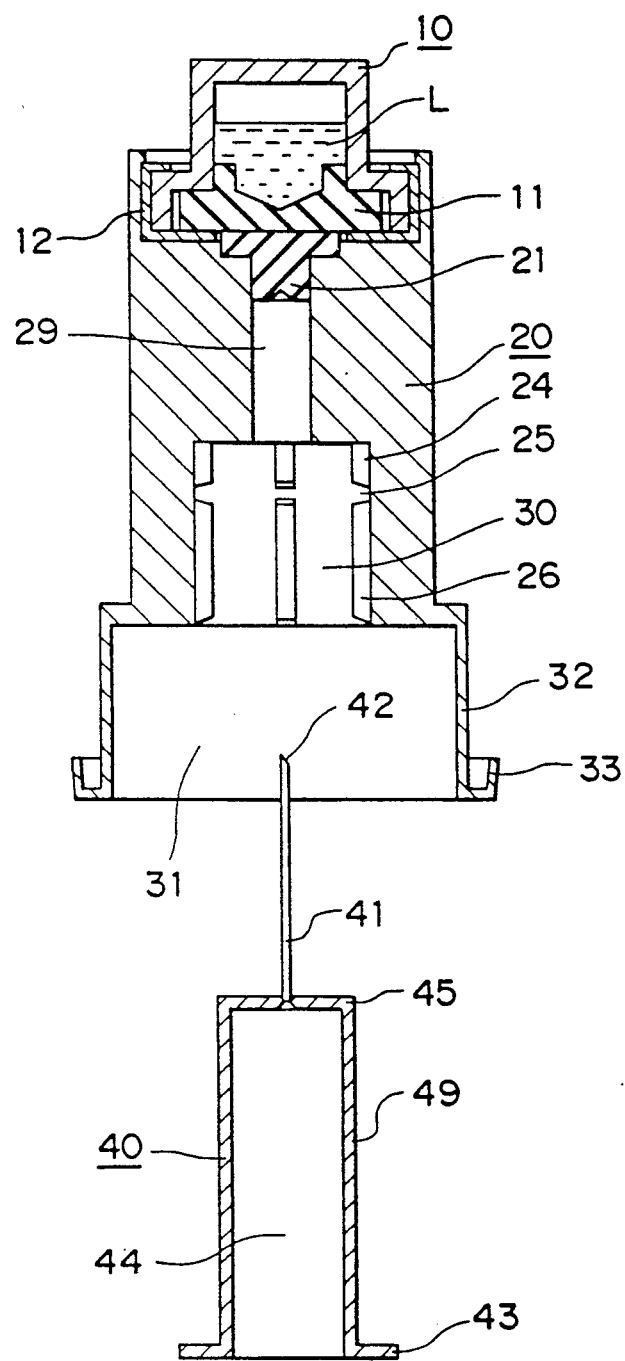
FIG. 16 is a sectional view showing a first step of assembling an injector to the housing in the embodiment of FIG. 1.
Figure 17:
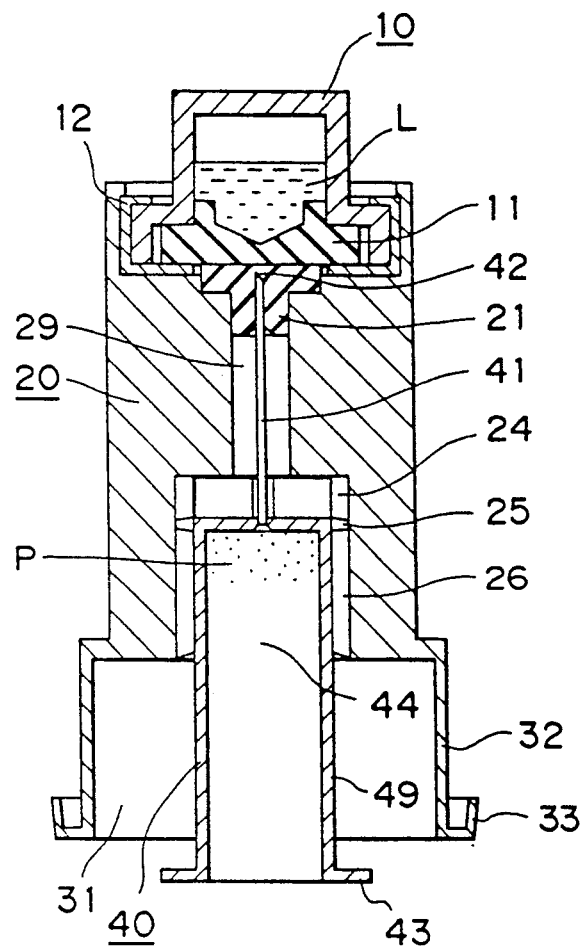
FIG. 17 is a sectional view showing a second step of assembling the injector to the housing in the embodiment of FIG. 1.
Figure 18:
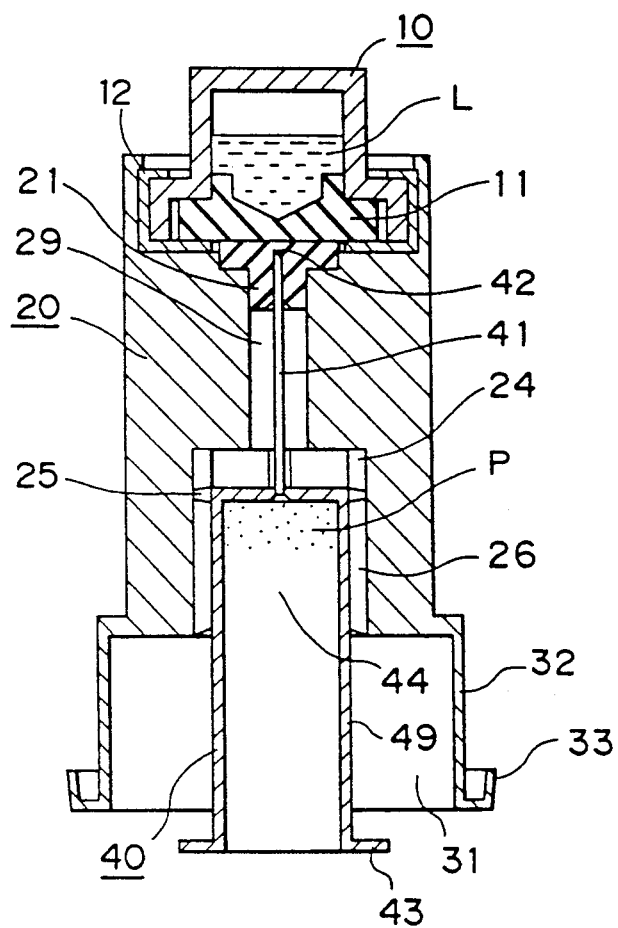
FIG. 18 is a sectional view showing a third step of assembling the injector to the housing in the embodiment of FIG. 1.
Figure 18:
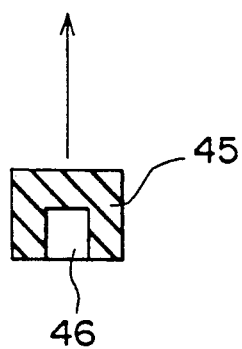
Figure 19:
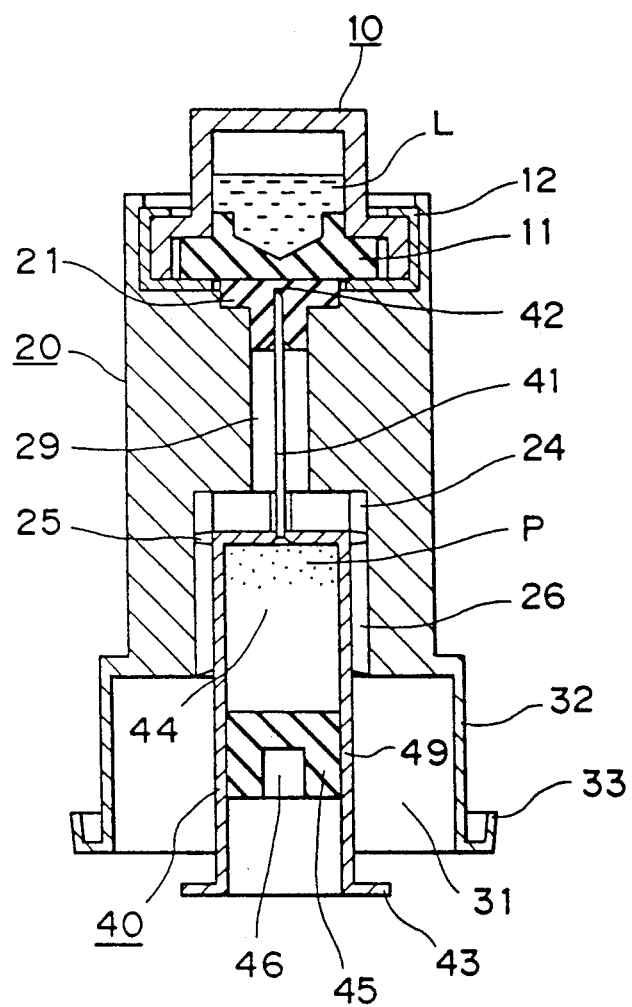
FIG. 19 is a sectional view showing a fourth step of assembling the injector to the housing in the embodiment of FIG. 1.
Figure 20:
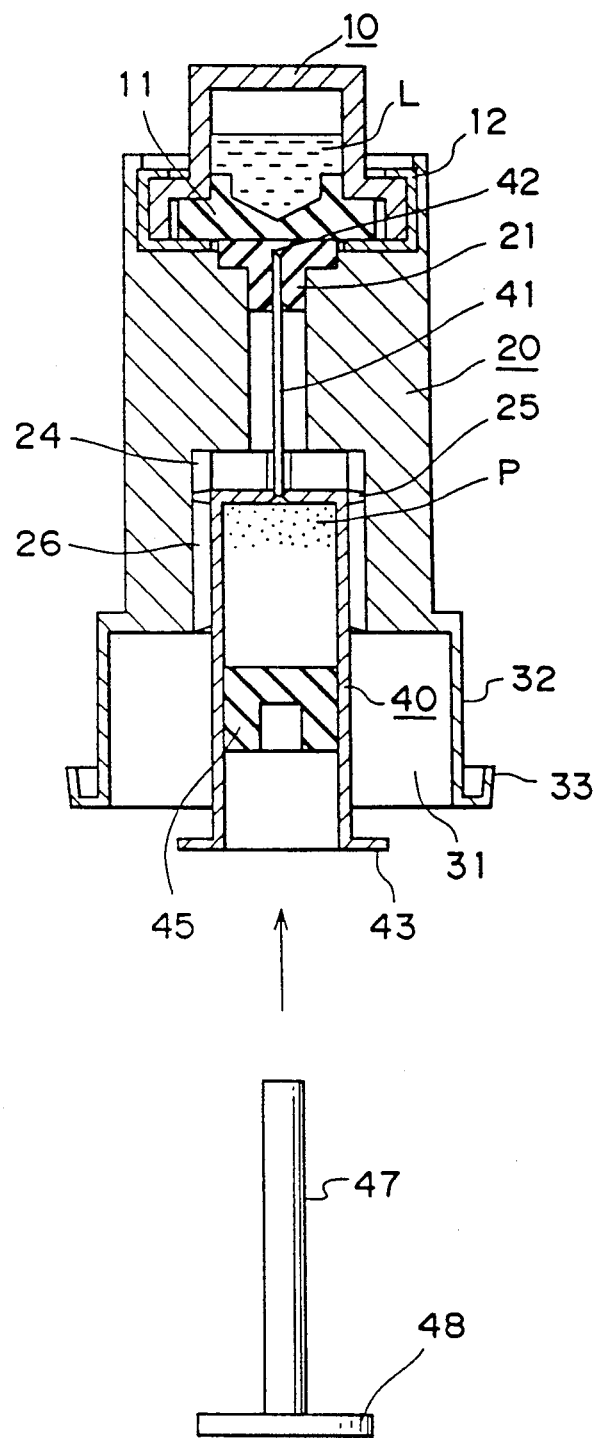
FIG. 20 is a sectional view showing a fifth step of assembling the injector to the housing in the embodiment of FIG. 1.
Figure 21:
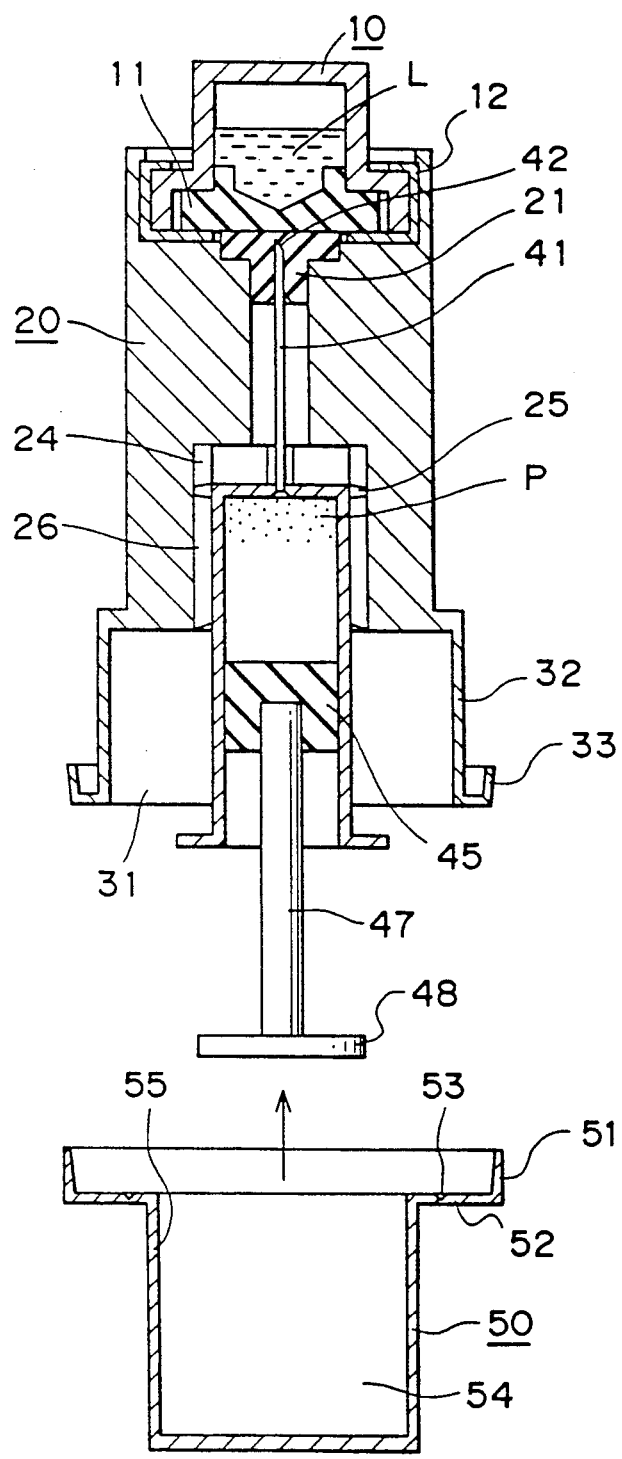
FIG. 21 is a sectional view showing a step of assembling a cover to the housing in the embodiment of FIG. 1.

FIG. 1 through FIG. 4 are sectional views showing the construction in the storage condition of the dual-chamber type syringe. FIG. 5 through FIG. 7 are sectional showing the using condition of the dual-chamber type syringe of FIG. 1. FIG. 8 through FIG. 21 are sectional views showing the sequential construction of the assembling condition of the dual-chamber type syringe of FIG. 1.

A dual-chamber type syringe shown in FIG. 1 is composed of a cylindrical housing 20, a second component container 10 provided at the top end of the housing 20, an injector 40 accommodated within a first chambers 30, 31 provided within the housing 20, a cover 50 for air tightly closing the chambers 30, 31 of the housing 20.

The second component container 10 is composed of a cup 14 for forming a second space chamber for enclosing the second liquid component L therein, a first seal member 11, a seal material 12 for securing both the cup 14 and member 11. The assembling operation is effected in the order of FIG. 8 through FIG. 12.

The housing 20 is composed of, from the upper portion to the lower portion, a mounting portion 27 of the second component container 10, an engagement portion 28 of the second seal member 21, a small diameter portion 29, a large diameter portion 30, a cavity portion 31 and a flange portion 33 formed in the end portion of the wall face 32 of the cavity portion 31. In the order shown in FIG. 13 through FIG. 15, the second seal member 21 is secured onto the engagement portion 28 and the second component container 10 is secured onto the mounting portion 27. The inner peripheral face of the large diameter portion 30 is provided serially with, from the upper portion to the lower portion, a short-sized second rib 24 for tightly tightening use, a gap portion 25, a long-sized first rib 26 for loosely tightening use. As shown in FIG. 1 and FIG. 5, the injector 40 is adapted to be detachably engaged respectively in the tightly tightened or loosely tightened condition with the ribs 24, 26 of the large diameter portion 30.

The injector 40 is composed of an injection cylinder 49 for forming a first space chamber 44 into which a first powder component P is inserted, an injection needle 41 provided on the top end 45 of the injection cylinder 49, a flange 43 provided at the lower end of the above injection cylinder 49, a plunger 45 which is provided for its free vertical, slidable operation in the lower end opening portion of the above injection cylinder 49 so as to air tightly close the first space portion 44, a rod 47 with a base 48 attached to it with the tip end being engaged into the hole portion 46 of the plunger 45 for slidably operating the plunger 45. In the order shown in FIG. 16 through FIG. 21, the injector 40 is mounted within the housing 20 with the tip end opening 42 of the injection needle 41 being thrust into the second seal member 21, and the outer face of the injection cylinder 49 being slidably engaged with the first rib 26 of the housing 20.

The cover 50 is composed of a receiving housing 55 for covering the injection cylinder 49 and the rod 47, an engagement flange 51 formed on the top end of the receiving housing 55 and adapted to air tightly close the cavity portion 31 of the housing 20, fixedly engaged with the flange portion 33 of the above described housing 20, a notch groove portion 53 for cutting use formed in the connection portion of the engagement flange 51 and the upper portion 52 of the receiving housing 55. The cover 50 is mounted on the housing 20 in a condition shown in FIG. 1. The cover 50 is forced to be raised upwards as shown in FIG. 5 so that the receiving housing 55 and the engagement flange 51 are easily cut in the groove portion 53 as shown in FIG. 5 to separate both the flange 51 and receiving housing 55.

The liquid component L is enclosed in the space chamber 15 of the second component container 10 by such a dual-chamber type syringe constructed as described hereinabove with the powder component P being air tightly closed in the space chamber 44 of the injection cylinder 49. The plunger 45 and the rod 47 of the injector 40 are air tightly covered with the cover 50 and the housing 20. During the using operation, the receiving housing 55 of the cover 50 is separated, cut from the engagement flange 51 with the raised groove portion 53 so as to push up the plunger 45. The injection needle 41 is penetrate through the seal members 11, 21. The liquid component L within the space chamber 15 of the container 10 is introduced into the space chamber 44 of the injection cylinder 49 from the tip end opening 42 inserted into the space chamber 15 of the second component container 10 so as to mix the powder component P.

The space chamber 15 of the second component container 10 is formed by a cup-shaped cup 14, a rubber made seal member 11 capable of thrusting for air tightly closing the opening portion of the cup 14 in the closed space for accommodating the liquid component L therein such as liquid solvent or the like as the component. The cup 14 and the seal member 11 are secured with an outer side seal material 12, is secured through a seal material such as a bonding agent or the like on the mounting portion 27 of the housing 20. The second component container 10 may be mounted with a clinch 23 of the tip end of the housing through a seal material on the mounting portion 27 of the housing 20.

The injection needle 41 is secured to the tip end of the injection cylinder 49. The rubber made plunger 45 is inserted for its free sliding operation into the rear end 45 opening portion of the injection cylinder 49. Solid (powder) medicine P which is the first component is filled therein. The injection needle 41 is inserted into the small diameter portion 29 of the housing 20. The tip end portion of the injection cylinder 49 is inserted into the large diameter portion of the housing 20.

The housing 20 has the large diameter portion 30 having a comparatively large inner diameter for accommodating the injection cylinder 49, a small diameter portion 29 provided above the large diameter portion 30 and adapted to accommodate the injection needle 41 of the injection cylinder 49. The cavity portion 31 of a larger diameter is provided in the lower end portion of the large diameter portion 30. The engagement portion 28 of the second seal member 21 and the mounting portion 27 of the second component container 10 are provided on the top portion of the small diameter portion 29. A plurality of first ribs 26 of comparatively long size are formed, in a portion into which the tip end portion of the injection cylinder 49 is inserted in the storage condition shown in FIG. 1, on the inner periphery of the large diameter portion 30. A plurality of second ribs 24 smaller slightly in inner diameter size than the first ribs 26 as far as the small diameter portion 29 in the gap portion 25 and comparatively short in size with the injection cylinder 49 being tightly tightened are formed on the top portion.

The rubber made second seal member 21 capable of penetrating is fixedly engaged into the top portion of the small diameter portion 29 of the housing 20 and the engagement portion 28. In the storage condition shown in FIG. 1, the tip end of the injection needle 41 of the injection cylinder 49 is thrust into the seal member 21 by the given size with the seal member 21 being not penetrated through.

The rod 47 is engaged into the plunger 45. The lower end portion of the injection cylinder 49 is covered air tightly with respect to the outer portion by the cavity portion 31 of the housing 20 and the cover 50 detachably secured in the cavity portion 31, including the plunger rod 47.

The cover 50 is cup-shaped of the receiving housing 55 having a chamber 54, as a whole, the engagement flange 51 is formed in the opening portion of the receiving housing 55. The engagement flange 51 is fixedly engaged with the flange portion 33 formed in the cavity portion 31 of the housing 20 and seals with respect to the outside of the plunger 45 including the injection cylinder 49 and the rod 47. The circle-shaped groove portion 53 on the side inner than the secured portion is formed on the inner side of the engagement flange 51 of the cover 50 and is easy to break in this portion. The engagement of the cover 50 with the flange portion 33 of the housing is bonded with a bonding agent or may be bonded with welding.

The procedures of a preparing operation in a case where the injection is effected from the above storage condition shown in FIG. 1 will be described hereinafter about FIG. 5 through FIG. 7.

The cover 50 depressed forwards from the condition of FIG. 1. Thus, the groove portion 53 formed in the cover 50 is broken. The plunger rod 47 depressed with the cover 50. The plunger 45 is depressed towards the upper portion of the injection cylinder 49. At this time, the space within the injection cylinder 49 is closed with the tip end of the injection needle 41 being sealed by the sealing member 21. The air within the space chamber 44 of the injection cylinder 49 is compressed so as to advance the injection cylinder 49 with the repulsion force. When the plunger 45 is pressed forwards to some extent, the injection cylinder 49 also slides on the portion of the second rib 24 within the housing 20 so as to move towards the tip end side within the housing 20. As shown in FIG. 5, the tip end face of the injection cylinder 49 reaches the terminal face of the large diameter portion 30 of the housing 20, so that the tip end opening 42 of the injection needle 41 penetrates through the seal members 21 and 11 so as to penetrate into the second component container 15. In this condition, gas within the injection cylinder 49, the housing 20 and the second component container 15 becomes compressed by the advance amount of the injection cylinder 49 and the plunger 45. The tip end portion of the broken cover 50 comes into contact against the end face portion of the hollow portion 31 of the housing 20 so as to stop the advance of the plunger 45 and the injection cylinder 49. In this condition, space corresponding to the amount of the first component is retained within the injection cylinder 49. The size of each portion is desired to be set in a condition where the tip end face of the injection cylinder 49 comes into contact against the terminal face of the large diameter portion 30 of the housing 20.

The broken cover 50 is removed, and the plunger rod 47 is rearwards restored so as to retreat the plunger 45. As shown in FIG. 6, the liquid component L within the second component container 15 is sucked into the injection cylinder 49 to mix it with the first component P for dissolving it. As the gas within the injection cylinder 49 and the second component container 15 is in a compressing condition in the condition of FIG. 5, the depression of the plunger 45 is stopped to effect the opening operation, and the plunger 45 is retreated automatically by the inner pressure. As the injection cylinder 49 is retained comparatively strictly by the second rib 24 within the housing 20, it does not retreat. At the retreating time of the plunger 45, the second component container 15 is positioned upwards. The liquid component L within the second component container 15 is absorbed automatically with the injection needle 41 so as to flow it into the injection cylinder 49.

Thereafter, the air venting operation within the injection cylinder 49 is effected. As shown in FIG. 7, the air venting operation is effected with the tip end of the injection needle 41 being inserted into the second component container 15. The mixed, dissolved medicine enters the second component container 15 to prevent it from being leaked outsides.

After the above operation, the injection cylinder 49, together with the injection needle 41 and the plunger 45, is withdrawn from the housing 20, thus allowing the immediate injection to be effected.

In the above described embodiment, the seal member 21 of the tip end opening portion of the housing 20 and the seal member 11 for closing the opening portion of the second component container 15 are provided as separate members. They may be integrated. By the separation of the seal members 21 and 11, terminal sterilization and assembling operations are simplified.

The fixing between the second component container 15 and the housing 20 is not necessarily required to use the seal material 12. For example, air tightness fixing can be effected with wind tightening or the like.

The first component medicine to be accommodated within the injection cylinder 49 may be, needless to say, liquid medicine especially without restriction to solid medicine.

Figure 22:
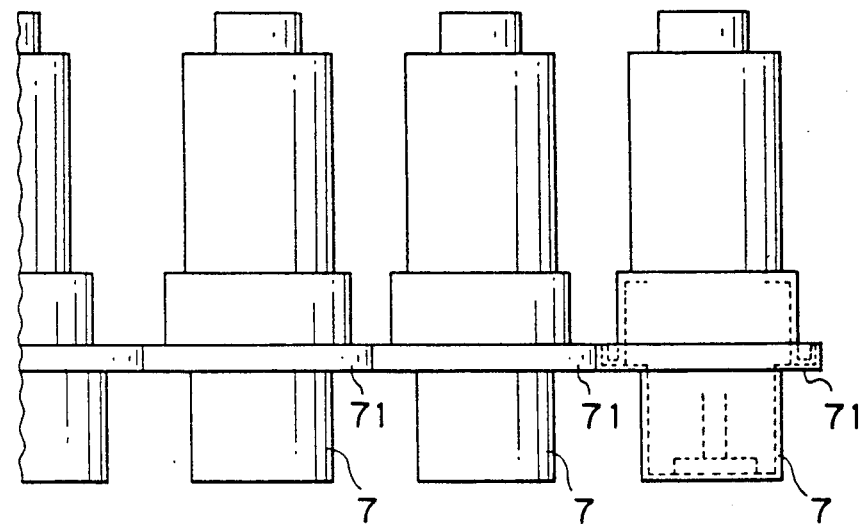
FIG. 22 is a front face view where the outer peripheries of the flange portions of the mutually adjacent covers in the modified embodiment of the present invention embodiment are mutually spliced weakly with each other.
Figure 23:
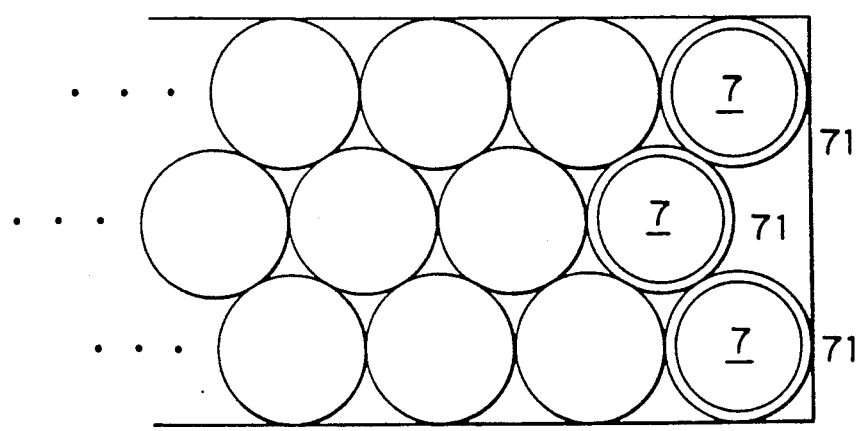
FIG. 23 is a plane view showing a packing condition in the condition of FIG. 22.

In the construction of the present invention, partial projection portion is formed specially on the periphery of the cover 50 or with the use of the projected portion of the flange portion 51 as shown in FIG. 22, the outer peripheral portion of the engagement flange 51 is manufactured in a condition where proper number of the outer peripheral portions is spliced weakly with each other without complete cutting of the mutual adjacent outer peripheral portions. In this condition, the other constructing members may be built in, shipped. In the assembling steps of the respective construction members, a flowing operation can be effected with a plurality of manufacturing lines being collected so that the handling operation can be simplified. As the packing condition may be made compact as shown in a plane view in FIG. 23, with an advantage point that space is not required for transportation and storage.

As is clear from the foregoing description, according to the arrangement of the present invention, the injection needle is secured to a tip end, and a first component is filled into the injection cylinder into which the plunger is inserted for its free sliding operation from the rear end opening portion. The tip end of the injection cylinder is inserted into its free sliding operation into the housing with which the seal member capable of thrusting into the tip end opening portion through. A second component container with the second component of the liquid being accommodated therein is air tightly engaged into the tip end portion of the housing across the above described seal member. A cover for air tightly covering the above described injection cylinder and plunger in cooperation with the housing is detachable with respect to the rear end opening portion of the housing Therefore, the injection cylinder, an injection needle and two components accommodated within are also air tightly sealed with respect to the open air. The whole apparatus including each component can be retained aseptically immediately before the prescribing operation, so that two components are not mixed with each other. Especially an injection needle is not prepared and is stored together with an injection cylinder aseptically. An assembling operation including the mixing resolution of two components and the injection needle at the prescribing preparation time is not necessary. Medical treatment workers can easily handle.

As the injection cylinder, the injection needle and the plunger are air tightly kept with respect to the outside, the transportation and the storage can be effected without use of the armored components, thus resulting in corresponding compactness.

The engagement can be effected air tightly with the housing with liquid component being accommodated within the second component container in the manufacturing step. Special members are not used. The manufacturing operation is easily effected. The terminal sterilization can be effected if necessary.

Effect the air venting operation within the injection cylinder with the second component container being engaged, and the medicine after the mixing resolution is not leaked outsides. Especially when the dangerous medicine is used, the effect is larger.

Many items demanded by this type of injector can be achieved. The disposable dual-chamber type syringes rich in practical use can be obtained.

Although the present invention has been fully described by way of example with reference to the accompanying drawings, it is to be noted here that various changes and modifications will be apparent to those skilled in the art. Therefore, unless otherwise such changes and modifications depart from the scope of the present invention, they should be construed as included therein.

What is claimed is:

1. A disposable dual-chamber syringe for use in separately accommodating a liquid and a medicine which are to be mixed with one another prior to injection, comprising:

an injection cylinder having a top end and an open bottom end;

an injection needle having a tip end and a base end, said base end being mounted to said top end of said injection cylinder;

a plunger axially slidably mounted within said injection cylinder and being adapted to retain a medicine in said injection cylinder;

a housing having an open bottom end for slidably receiving said injection cylinder, and a top end;

a seal member mounted in said top end of said housing and being adapted to be penetrated by said tip end of said injection needle;

a second component container mounted to said top end of said housing, said second component container, together with said seal member, forming a sealed chamber for containing the liquid; and a cover fixed to said bottom end of said housing to cover and seal said open bottom end thereof in an air tight manner, said cover and said housing defining a housing chamber within which said injection cylinder is enclosed.

2. A disposable dual chamber syringe as recited in claim 1, wherein
said cover is generally cup-shaped with an upwardly opening top end, a flange portion being formed about said top end and defining a means for securing said cover to said bottom end of said housing in an air tight manner.

3. A disposable dual chamber syringe as recited in claim 2, wherein
said flange portion has an annular groove formed therein to define a frangible means for allowing the cup-shaped portion of said cover to be pressed upwardly and be broken away from an outer part of said flange portion.

4. A disposable dual chamber syringe as recited in claim 1, wherein
said housing chamber defined by said cover by said housing has a cavity portion defined in a lower portion thereof, and a communication portion extending from said cavity portion toward said top end of said housing to allow for communication between said injection cylinder when disposed in said housing and said sealed chamber.

5. A disposable dual chamber syringe as recited in claim 4, wherein
said seal member comprises a first seal element mounted in an upper end of said communication portion and a second seal element mounted atop said first seal element and in a bottom end of said second component container.

6. A disposable dual-chamber syringe for use in separately accommodating a liquid and a medicine which are to be mixed with one another prior to injection, comprising:
a cylindrical housing having an upper portion and a lower portion, and including a second mounting portion at said upper portion, and firs and third mounting portions at said lower portion, said first and second mounting portions being in communication with one another;
a second component chamber, mounted to said housing at said second mounting portion, for containing the liquid;
a needle penetrable seal member sealingly closing a lower end of said second component chamber;
an injector, slidably mounted to said first mounting portion for sliding movement between first and second positions, including an injection cylinder for receiving the medicine, a plunger slidably mounted in said injection cylinder for sealing the medicine in said injection cylinder, and an injection needle mounted to said injection cylinder for penetrating said seal member; and
a cover detachably mounted to said third mounting portion for covering said injector in an air tight manner, said cover including a frangible means for allowing a first portion of said cover to be broken away from a second portion of said cover, pushed upwardly to press said plunger upwardly, cause said injector to be moved from said first position to said second position, and cause said injection needle to penetrate through said seal member to allow the medicine and the liquid to be mixed through said needle, when said first portion of said cover is pressed upwardly.

7. A disposable dual chamber syringe as recited in claim 6, wherein
said first mounting portion comprises a guide means for guiding said injector between said first and second positions; and
said guide means comprises a plurality of first-stage ribs for guiding said injector prior to said first portion of said cover being broken away from said second portion of said cover, and a plurality of second-stage ribs respectively aligned with said plurality of first-stage ribs for guiding said injector after said first portion of said cover has been broken away from said second portion of said cover and pressed upwardly.

8. A disposable dual chamber syringe as recited in claim 7, wherein
said first-stage ribs are longer than said second-stage ribs.

* * * * *